US 6,727,713 B1

(12) United States Patent
Choi et al.

(10) Patent No.: US 6,727,713 B1
(45) Date of Patent: Apr. 27, 2004

(54) ELECTRONIC COMPONENT LEAD INSPECTION DEVICE

(75) Inventors: Jong-Ju Choi, Seoul (KR); Dong-Sik Jang, Seoul (KR)

(73) Assignee: ViewWell Co., Inc., Seoul (KR)

(*) Notice: Subject to any disclaimer, the term of this patent is extended or adjusted under 35 U.S.C. 154(b) by 0 days.

(21) Appl. No.: 09/786,357

(22) PCT Filed: Sep. 16, 1999

(86) PCT No.: PCT/KR99/00557

§ 371 (c)(1),
(2), (4) Date: Mar. 14, 2001

(87) PCT Pub. No.: WO00/16076

PCT Pub. Date: Mar. 23, 2000

(30) Foreign Application Priority Data

Sep. 17, 1998 (KR) .......................... 1998-38479
Aug. 3, 1999 (KR) .......................... 1999-31796

(51) Int. Cl.$^7$ .............................. G01R 31/308
(52) U.S. Cl. ................... 324/753; 324/765; 324/158.1
(58) Field of Search .............................. 324/158.1, 765, 324/753; 348/125, 126; 382/145

(56) References Cited

U.S. PATENT DOCUMENTS 4,739,175 A    4/1988  Tamura
5,114,229 A    5/1992  Hideshima
5,138,180 A *  8/1992  Yamanaka ............. 250/559.07
5,406,372 A    4/1995  Yodanovic et al.
6,072,898 A *  6/2000  Beaty et al. ................. 382/146
6,195,165 B1 * 2/2001  Sayegh ....................... 356/613

FOREIGN PATENT DOCUMENTS

JP        10-227622 A    8/1998
WO        WO 97/28420 A  8/1997

* cited by examiner

Primary Examiner—Kamand Cuneo
Assistant Examiner—Tung X. Nguyen
(74) Attorney, Agent, or Firm—Bacon & Thomas, PLLC

(57) ABSTRACT

An electronic component lead inspection device, the device comprising: a pickup header for picking up an electronic component package to move same; a light source for illuminating a light to the electronic component package; a acquiring unit for acquiring an image of the electronic component package underneath a travelling passage of the electronic component package; a control unit for outputting an image signal of the electronic component package acquired by the acquiring unit; and an inspecting and displaying unit for receiving the image signal of the electronic component package output from the control means to inspect and display the image of the electronic component package, such that the electronic component packages can be all inspected on real time, while the electronic component packages are being moved, inspected and produced.

9 Claims, 13 Drawing Sheets

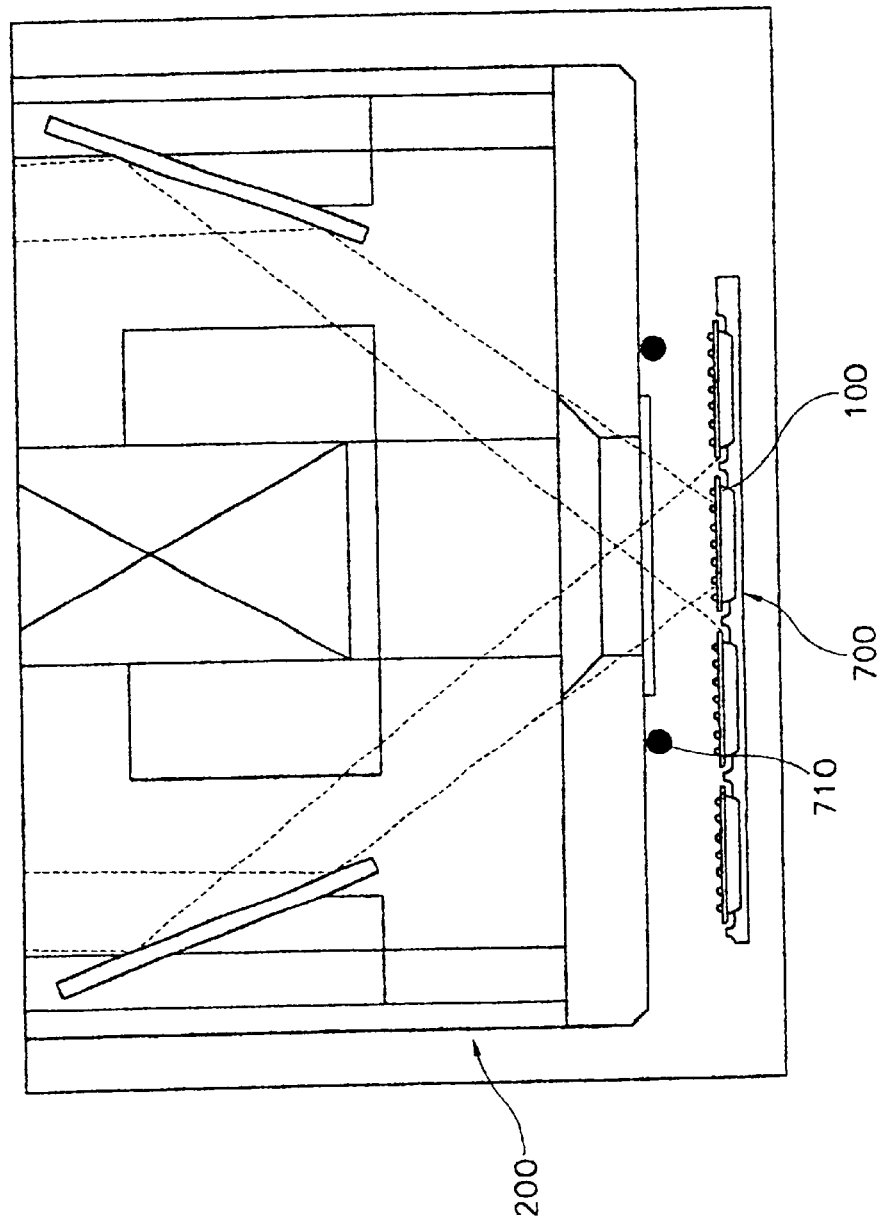

ELECTRONIC COMPONENT LEAD INSPECTION DEVICE

BACKGROUND OF INVENTION

1. Field of the Invention

The present invention relates to an electronic component lead inspection device, and more particularly to an electronic component lead inspection device adapted to acquire an image of an electronic component lead and to inspect whether the electronic component leads are good or bad according to the acquired image.

2. Description of the Prior Art

Various types of electronic component lead inspection devices are disclosed. One of them is illustrated in FIG. 1, where, an integrated circuit package 1 positioned on a pedestal (not shown) formed at a glass plate 2 is inspected by light from four light sources (3, 4, 5, 6) located at four corners, which sequentially illuminate the package 1 to check if electronic component leads are good or bad.

In other words, when one light source 3 illuminates light, images of the electronic component lead from two directions can be obtained, such that when four light sources (3, 4, 5, 6) sequentially illuminate light, images on position of electronic component leads in four directions can be obtained. Inspection procedures of electronic component lead by the electronic component lead inspection device thus described will be explained as below:

An electronic component package on a tray is put on a pickup header and moved to an inspection position, and the electronic component package is put on a pedestal and pressed. Light is sequentially illuminated on the electronic component package laid on the pedestal to obtain an image on a position of electronic component lead in four directions.

Then, a pickup header lifts the electronic component package and puts it on the tray to thereby finish an inspection procedure of electronic component lead against one electronic component package.

However, there is a problem in the electronic component lead inspection device thus described in that an electronic component package should always maintain a fixed state to get an accurate image information on electronic component leads while images of the electronic component lead in four directions are continuously acquired.

Furthermore, there is another problem in that so the pickup header moves the electronic component package horizontally and vertically, mechanical driving time is much consumed and the probability of electronic component lead being damaged is high while the pickup header is driven. There is still another problem in that an image should be sequentially input at least more than twice to thereby take stand still times in acquiring images. There is still further problem in that inspection items such as mold damage, mold thickness, mold angle, shoulder length, shoulder angle and the like cannot be inspected.

Meanwhile, in an electronic component lead inspection device according to another prior art, a prism and a reflecting mirror are used, as illustrated in FIGS. 2a, to enlarge twice the image of the electronic component lead and to divide the image into two for view in up-and-down positions, as illustrated in FIG. 2b.

Inspection procedures of electronic component lead by the electronic component lead inspection device according to second prior art will be described as under:

An electronic component package on a tray is picked up by a pickup header, flipped by a mechanical method and is moved to inspection position. The flipped electronic component package is put on a pedestal while the pickup header is moved from the inspection position to an original position. The electronic component package is rotated four times per direction of the electronic component lead to obtain images in four directions while the electronic component package is laid on the pedestal. Next, the electronic component package is picked up by the pickup header, flipped by a mechanical method and moved on a tray, by which, an inspection procedure of an electronic component lead against one electronic component package is finished.

However, there is a problem in the electronic component lead inspection device thus described in that the pedestal should accurately rotate the electronic component package according to each direction of the electronic component lead, and if the pedestal cannot rotate the electronic component package at an exact angle or there occurs any vibration, an accurate inspection of the electronic component lead cannot be performed.

Furthermore, there is another problem in that the pickup header moves the electronic component package horizontally and vertically and rotates same, a mechanical driving time is much consumed and the probability of the electronic component lead being damaged is high while the pickup header is driven. There is still another problem in that an image should be sequentially acquire at least more than twice to thereby take lots of times in acquiring images. There is still further problem in that inspection item such warpage, mold damage and the like cannot be performed.

Meanwhile, in an electronic component lead inspection device according to a third prior art, four cameras (11, 12, 13, 14) are used, as shown in FIG. 3, to acquire each side view of an electronic component package 15 and to check whether an electronic component leads are good or bad. Inspection procedures of electronic component lead by the electronic component lead inspection device according to the third prior art will be described as follows:

An electronic component package on a tray is picked up by a pickup header, moved to an inspection position and laid on a pedestal. Four cameras acquire each side of the electronic component package while the electronic component package is laid on the pedestal. Next, the electronic component package is lifted by the pickup header to thereafter be laid on the tray, by which the inspection procedure of the electronic component lead against one electronic component package is finished.

However, there is a problem in the third electronic component lead inspection device thus described in that a lead portion of the electronic component package gets in touch with the pedestal to thereby incur a damage to the electronic component lead.

Furthermore, there is another problem in that, because the pickup header moves the electronic component package vertically and horizontally, a mechanical driving time is much consumed and the probability of electronic component lead being damaged is high while the pickup header is driven.

There is still another problem in that inspection items such as warpage, foot angle, mold damage, mold thickness, mold angle, shoulder length, shoulder angle and like cannot be performed.

SUMMARY OF THE INVENTION

Conclusively, there are lots of problems in the electronic component lead inspection devices thus described according to the prior arts in that frequency of mechanical movement is increased in order to inspect the electronic component package on a particular inspection position, such that the electronic component packages being produced cannot be inspected on real time. There is another problem in that the probability of the electronic component leads being damage is high. There is still another problem in that there may be items that cannot be inspected.

Accordingly, the present invention is disclosed to solve the aforementioned problems and it is an object of the present invention to provide an electronic component lead inspection device adapted to inspect electronic component package while they are moved so that the electronic component package being produced can be inspected on real time to thereby incur no damages to electronic component lead.

It is another object of the present invention to provide an electronic component lead inspection device adapted to accurately inspect inspection items impossible to be inspected in the prior arts and configured to be easily coupled for use to existing electronic component device according miniaturization and shortened mechanical control time.

In accordance with the objects of the present invention according to a first embodiment thereof, there is provided an electronic component lead inspection device, the device comprising:

a pickup header for picking up an electronic component package to move same;

a light source for illuminating a light to the electronic component package;

acquiring means for acquiring an image of the electronic component package underneath a travelling passage of the electronic component package;

control means for outputting an image signal of the electronic component package acquired by the acquiring means; and inspecting and displaying means for receiving the image signal of the electronic component package output from the control means to inspect and display the image of the electronic component package.

In accordance with the objects of the present invention according to a second embodiment thereof, there is provided an electronic component lead inspection device, the device comprising:

a pickup header for picking up an electronic component package to move same;

a reflecting plate attached to the pickup header;

a light source for illuminating a light to the reflecting plate;

acquiring means for acquiring an image of the electronic component package underneath a travelling passage of the electronic component package;

control means for outputting an image signal of the electronic component package acquired by the acquiring means; and inspecting and displaying means for receiving the image signal of the electronic component package output from the control means to inspect and display the image of the electronic component package.

In accordance with the objects of the present invention according to a third embodiment thereof, there is provided an electronic component lead inspection device, the device comprising:

a pickup header for picking up an electronic component package to move same;

a reflecting plate attached to the pickup header;

a first light source for illuminating a light to the reflecting plate;

a second light source for illuminating a light to the electronic component package;

acquiring means for acquiring an image of the electronic component package underneath a travelling passage of the electronic component package;

control means for controlling the first light source to illuminate a light if the electronic component package is a gull wing type electronic component package and for controlling the second light source to illuminate a light if the electronic component package is a ball grid array type electronic component package and for outputting an image signal of the electronic component package acquired by the acquiring means; and inspecting and displaying means for receiving the image signal of the electronic component package output from the control means to inspect and display the image of the electronic component package.

In accordance with the objects of the present invention according to a fourth embodiment thereof, there is provided an electronic component lead inspection device, the device comprising:

a tray for moving an accommodated electronic component;

a light source for illuminating a light to the electronic component package;

acquiring means for acquiring an image of the electronic component package above a travelling passage of the electronic component package;

control means for outputting an image signal of the electronic component package acquired by the acquiring means; and inspecting and displaying means for receiving the image signal of the electronic component package output from the control means to thereby inspect and display the image of the electronic component package.

BRIEF DESCRIPTION OF THE DRAWINGS

For fuller understanding of the nature and objects of the invention, reference should be made to the following detailed description taken in conjunction with the accompanying drawings in which:

FIG. 7 is an enlarged view of principal parts of an electronic component lead inspection device according to the fourth embodiment of the present invention;

DETAILED DESCRIPTION OF THE INVENTION

Now, preferred embodiment of the present invention will be described in detail with reference to the accompanying drawings.

Figure 1:
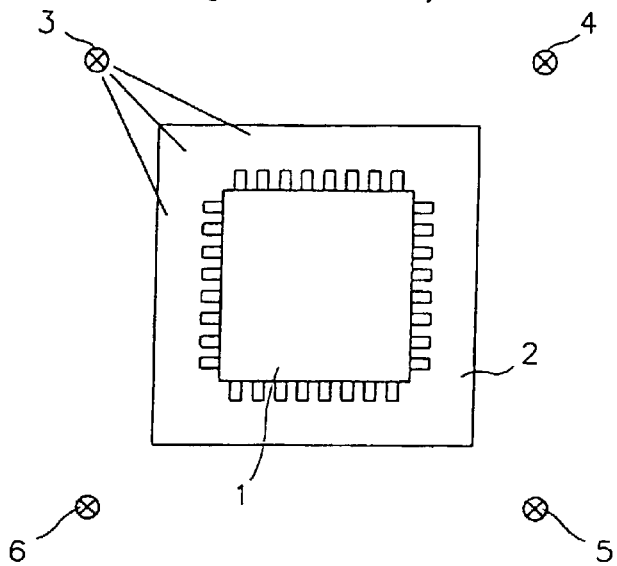
FIG. 1 is a schematic diagram of an electronic component lead inspection device according to the prior art.
Figure 2A:
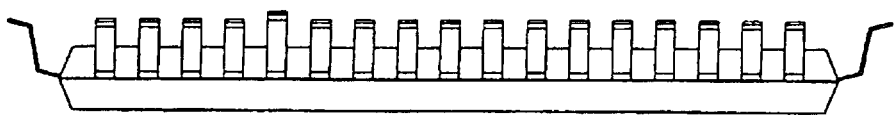
FIGS. 2a and 2b are schematic views of electronic component lead in images acquired by another electronic component lead inspection device according to the prior art.
Figure 2B:
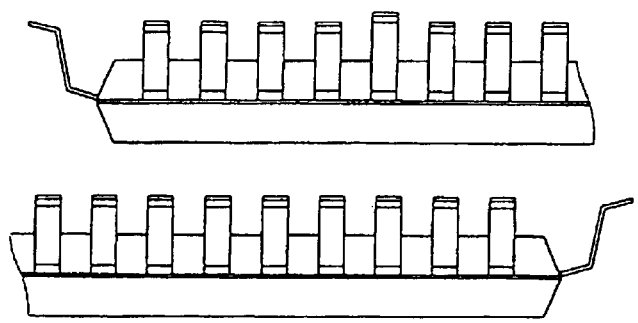
Figure 3:
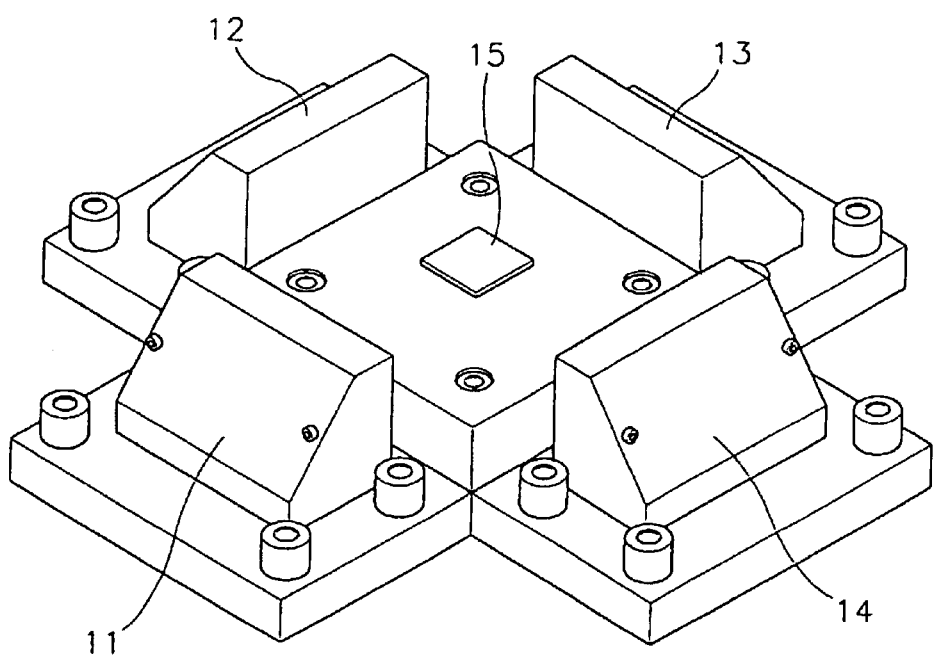
FIG. 3 is a schematic diagram of a still another electronic component lead inspection device according to the prior art.
Figure 4:
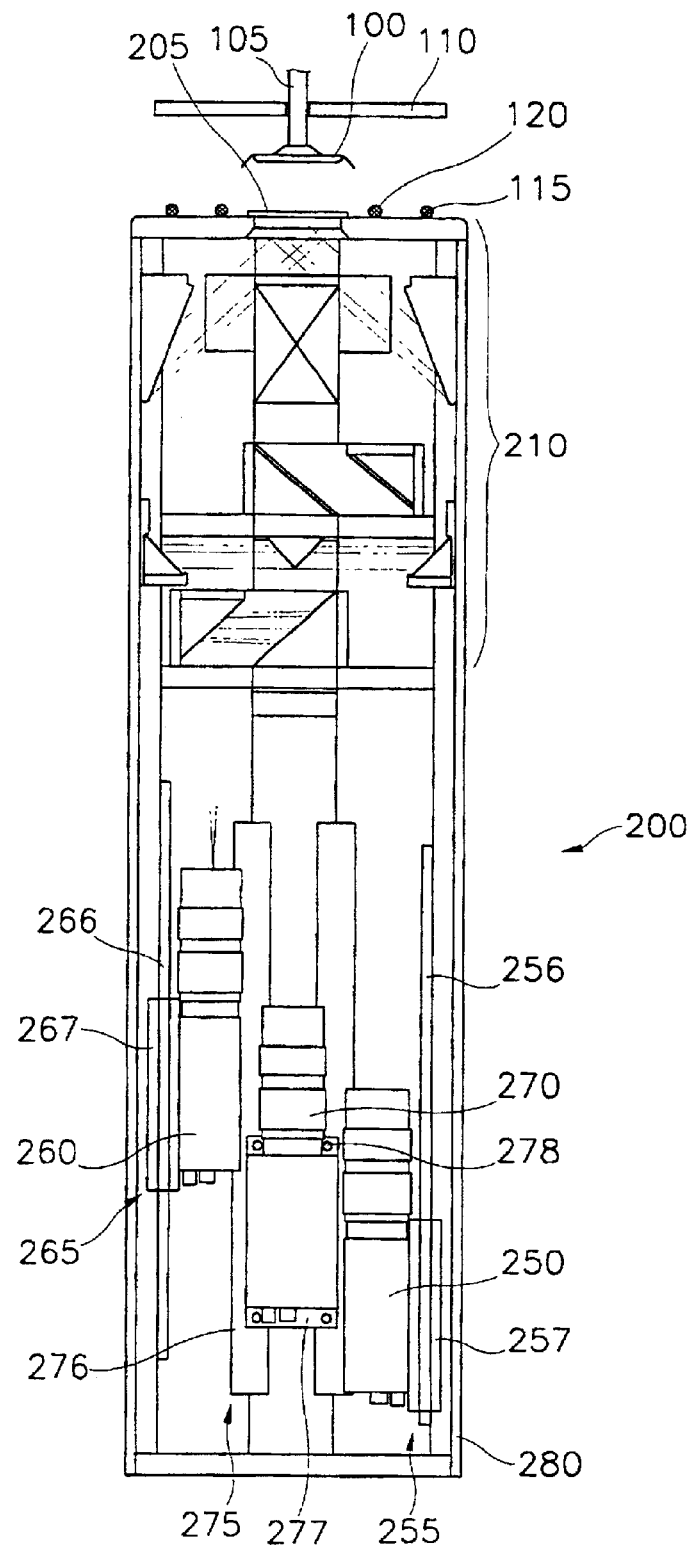
FIG. 4 is a schematic diagram of an electronic component lead inspection device according to the first, second and third embodiments of the present invention.
Figure 5:
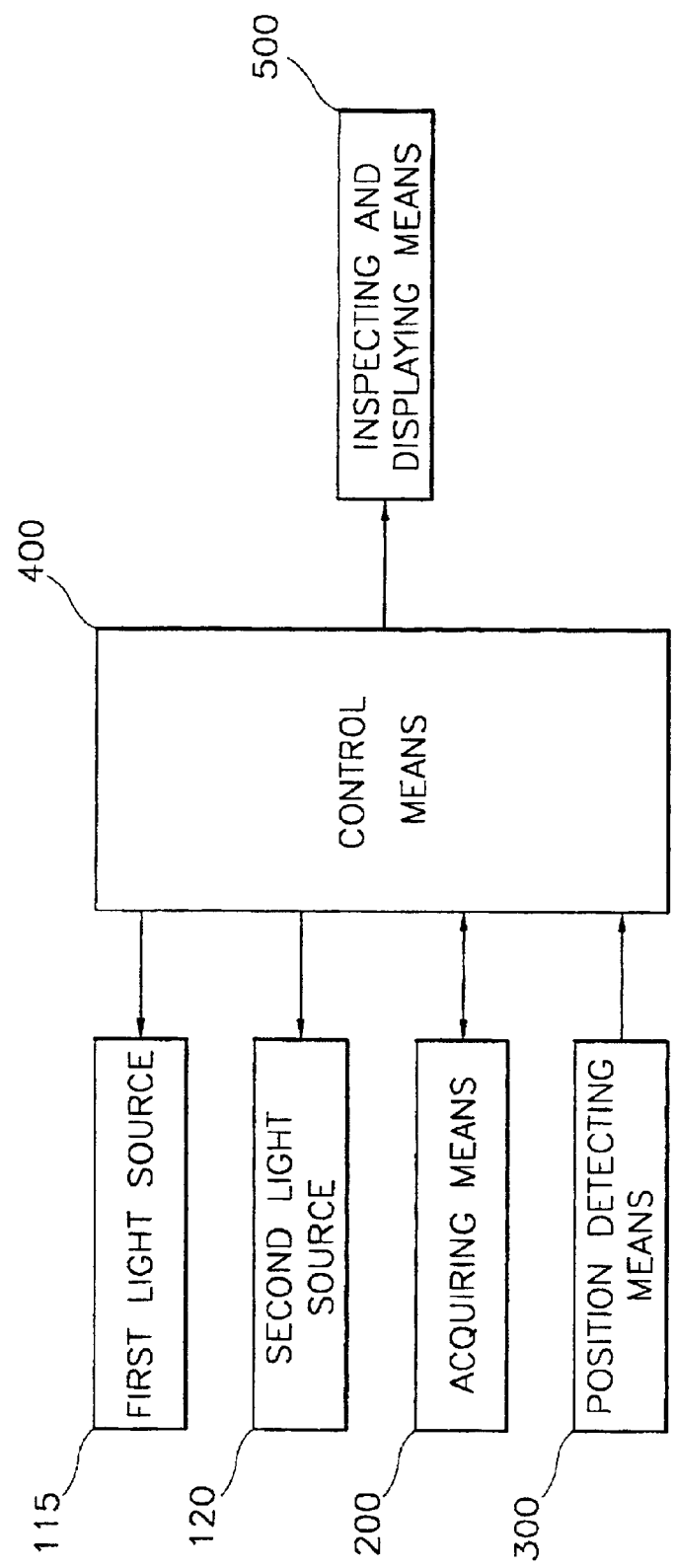
FIG. 5 is a control block diagram of an electronic component lead inspection device according to the first, second and third embodiments of the present invention.
Figure 6:
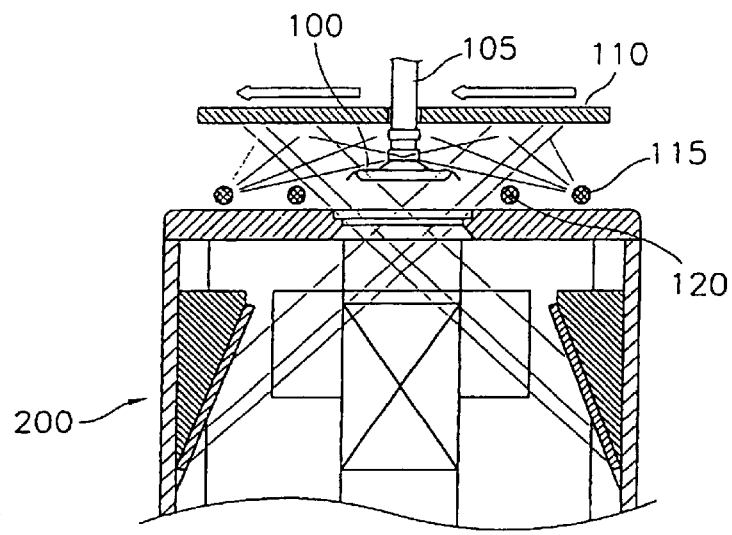
FIG. 6 is an enlarged view of principal parts of an electronic component lead inspection device according to the first, second and third embodiments of the present invention.
Figure 8:
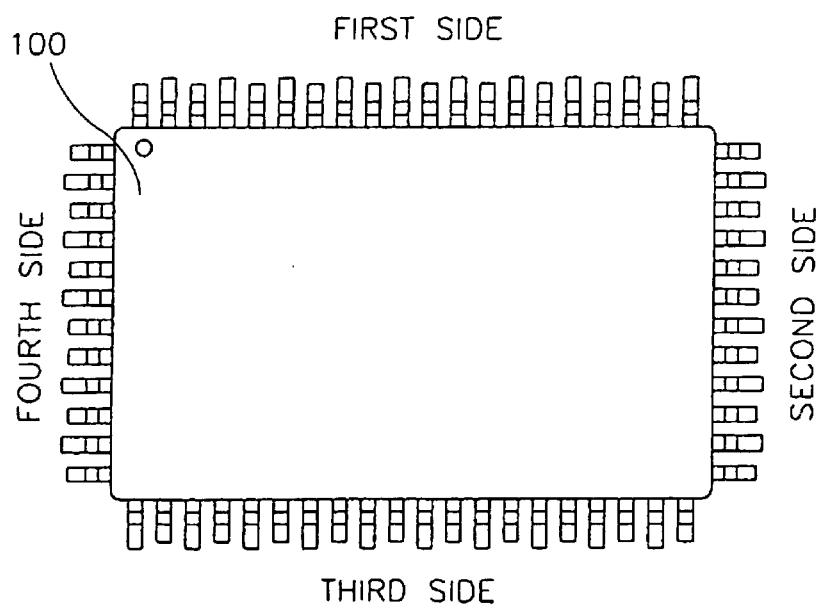
FIG. 8 is plan of a conventional gull wing type electronic component package.

FIG. 4 is a schematic sectional view of an electronic component lead inspection device according to the first, second and third embodiments of the present invention and FIG. 5 is a control block diagram of an electronic component lead inspection device according to the first, second and third embodiments of the present invention while FIG. 6 is an enlarged view of principal parts of an electronic component lead inspection device according to the first, second and third embodiments of the present invention.

As illustrated in FIGS. 4, 5 and 6, an electronic component lead inspection device according to the first, second and third embodiments of the present invention includes a pickup header 105, a reflecting plate 110, a first light source 115, a second light source 120, acquiring means 200, position detecting means 300, control means 400 and inspecting and displaying means 500.

The pickup header 105 serves to pick up an electronic component package 100 to horizontally move same, and the reflecting plate 110 attached to the pickup header 105 is painted at a bottom surface thereof with material such as irregular reflection paint for irregularly diffusing the light.

The first light source 115 illuminates a light to the reflecting plate 110 according to control of the control means 400 and the second light source 120 illuminates a light to the electronic component package 100 being horizontally moved by the pickup header 105 according to control of the control means 400, where, by way of example, the first and second light source 115 and 120 can be made by utilizing a light emitting diode (LED).

The acquiring means 200, disposed underneath a travelling passage of the electronic component package 100 being horizontally moved by a pickup header 105, serves to acquire an image of the electronic component package 100 to output same to the control means 400.

Furthermore, the acquiring means 200 is provided thereon with a transparent glass plate 205 for passing an image of the electronic component package 100 being horizontally moved by the pickup header 105 but for preventing foreign objects such as dust, mold flesh and the like from entering the acquiring means 200.

The position detecting means 300 detects a position of the electronic component package 100 to output to the control means 400 a signal that the electronic component package 100 has arrived at acquiring position. The position detecting means may be arranged at one side of an electronic component lead inspection device according to the present invention, or may be installed at an apparatus for driving the pickup header 105.

The control means 400 controls the first light source 115 to illuminate a light toward the reflecting plate 110 when a signal is input from the position detecting means 300 that the electronic component package 100 has reached the acquiring position in case the electronic component package 100 being horizontally moved by the pickup header 105 is a gull wing type electronic component package. The control means 400 controls the second light source 120 to illuminate a light toward the electronic component package when a signal is input from the position detecting means 300 that the electronic component package 100 has arrived at the acquiring position in case the electronic component package 100 being horizontally moved by the pickup header 105 is a ball grid array (BGA) type electronic component package.

Furthermore, the control means 400 receives an image signal of the electronic component package 100 acquired by the acquiring means 200 to output same to the inspecting and displaying means 500, where, the inspecting and displaying means receives the image signal of the electronic component package 100 output from the control means 400 to inspect and display the image of the electronic component package 100.

Although it is not illustrated in the drawings, it is preferable that an air blower is provided in order to eliminate dust, mold flesh and the like accumulated on the glass plate 205 mounted above the acquiring means 200.

FIG. 7 is an enlarged view of principal parts of an electronic component lead inspection device according to the fourth embodiment of the present invention. In comparison with the first, second and third embodiments of the present invention, there is no difference in the fourth embodiment of the present invention but rather identical to the first, second and third embodiments, except that a tray 700 moving by being coupled to separate transfer means instead of a pickup header moves the electronic component package still accommodated on the tray 700, and the acquiring means 200 is mounted on a travelling passage of the electronic component passage and only a light source 710 is used for illuminating a light to the electronic component package moved by the tray 700.

At this time, if the electronic component package is a BGA type electronic component package, it is being inspected in a flipped-over state, and if a gull wing type electronic component package, it is inspected with a lead portion thereof facing downwards.

Meanwhile, the acquiring means 200 includes, as illustrated in FIG. 4, image transfer means 210 and first, second and third cameras 250, 260 and 270, where the image transfer means 210 serves to transfer a bottom view image of the electronic component package 100 to the first camera 250 to allow the bottom view image of the electronic component package 100 to be acquired by the first camera 250, and to transfer images of a first side view and a third side view of the electronic component package 100 to the second camera 260 to allow the images to be acquired by the second camera 260, and to transfer images of a second side view and a fourth side view of the electronic component package 100 to the third camera 270 to allow the images to be acquired by the third camera 270.

Furthermore, the acquiring means 200 is provided with first, second and third height adjusting means 255, 265 and 275 for adjusting respective heights of the cameras 250, 260 and 270, where, the first, second and third height adjusting means 255, 265 and 275 include guide rails 256, 266 and 276 formed at one side of a housing 280, guide plates 257, 267 and 277 formed integrally with the first, second and third cameras 250, 260 and 270 for vertically moving the first, second and third cameras 250, 260 and 270 along the guide rails 256, 266 and 276, and fixing means 278 for fixing the guide plates 257, 267 and 277 to the guide rails 256, 266 and 276 to thereby fix positions of the first, second and third cameras 250, 260 and 270.

Although FIG. 4 illustrates only the fixing means 278 of the third height adjusting means 276, each fixing means of the first and second height adjusting means 255 and 265 has the same structure as the fixing means 278 of the third height adjusting means 275. The fixing means 278 is provided with a hole (not shown) formed at the guide plate 277, and the hole is formed at an inner periphery thereof with a female screw (not shown) through which a male screw (not shown) passes for screw engagement, and by which the guide plate 277 can be fixed to the guide rail 276.

At this time, it should be apparent that the same effect can be accomplished by utilizing a reflecting mirror and a prism to adjust a height of a transfer passage of an image instead of using the height adjusting means 255, 265 and 275 to adjust the heights of the cameras.

Figure 9:
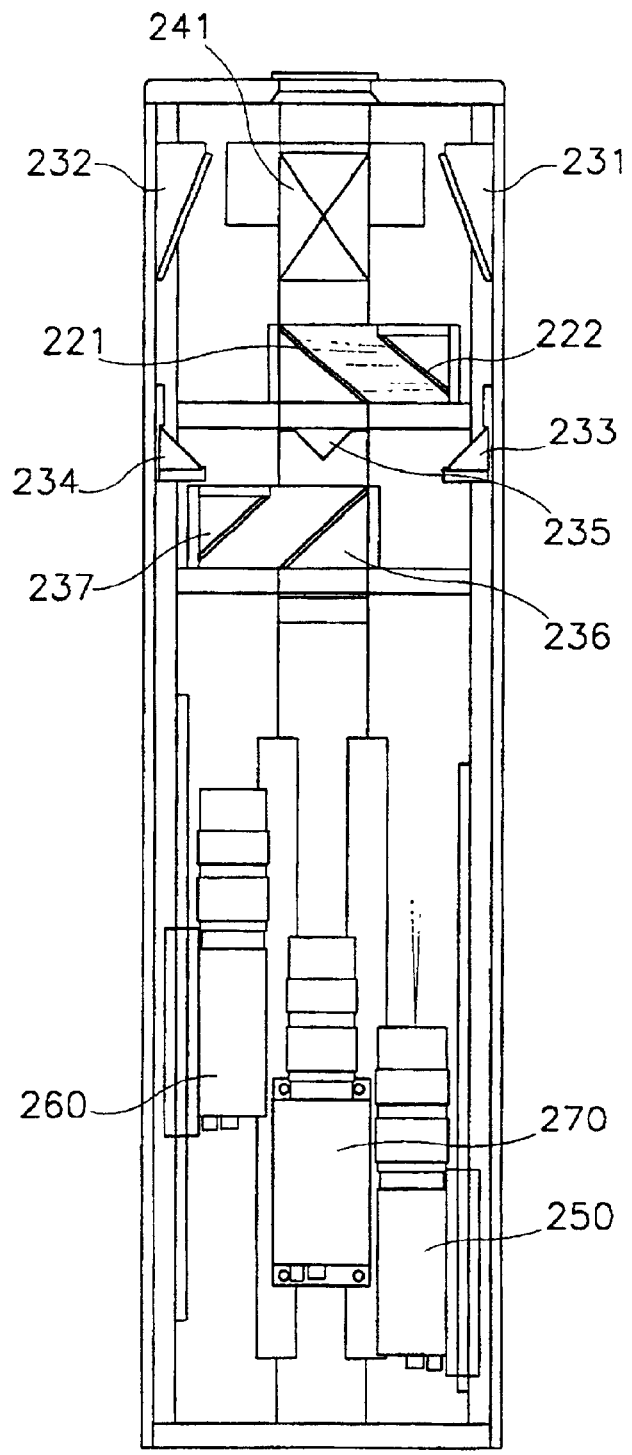
FIG. 9 is a drawing for illustrating passages where a bottom view image of an electronic component lead is transmitted in acquiring means according to the first embodiment of the present invention.
Figure 10:
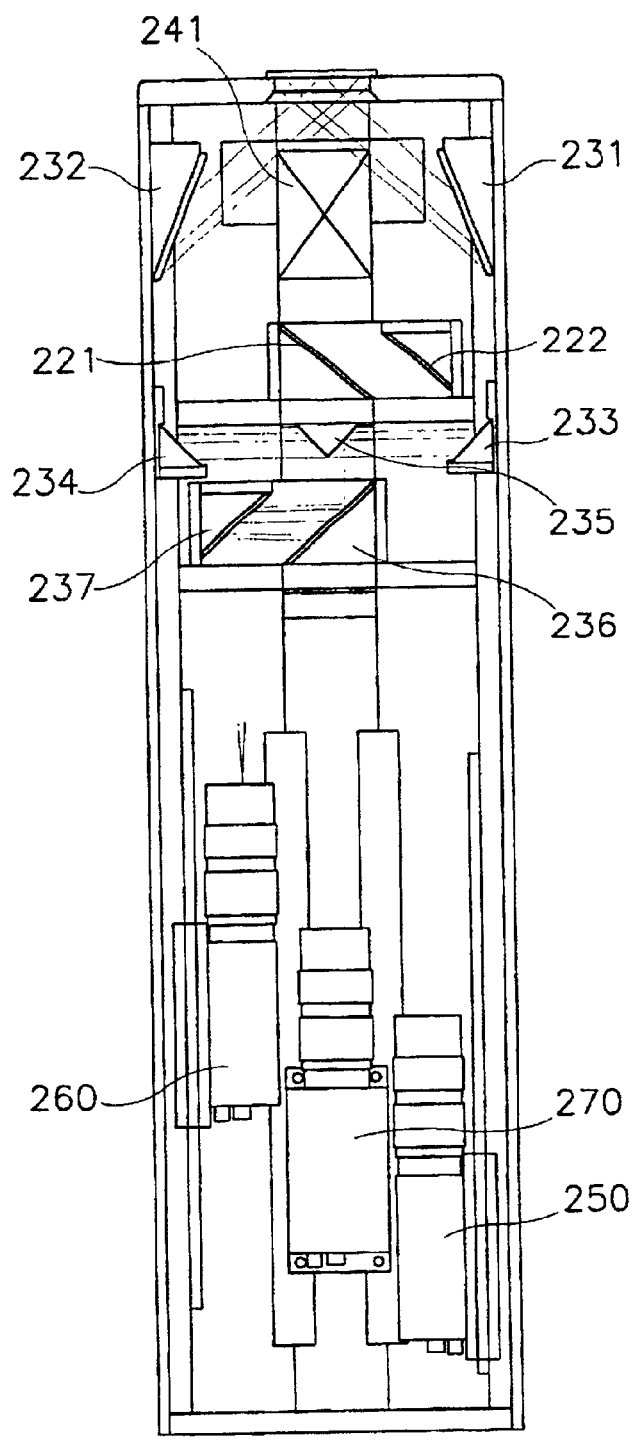
FIG. 10 is a drawing for illustrating passages where images of a first side view and a third side view of an electronic component lead are transmitted in acquiring means according to the first embodiment of the present invention.
Figure 11:
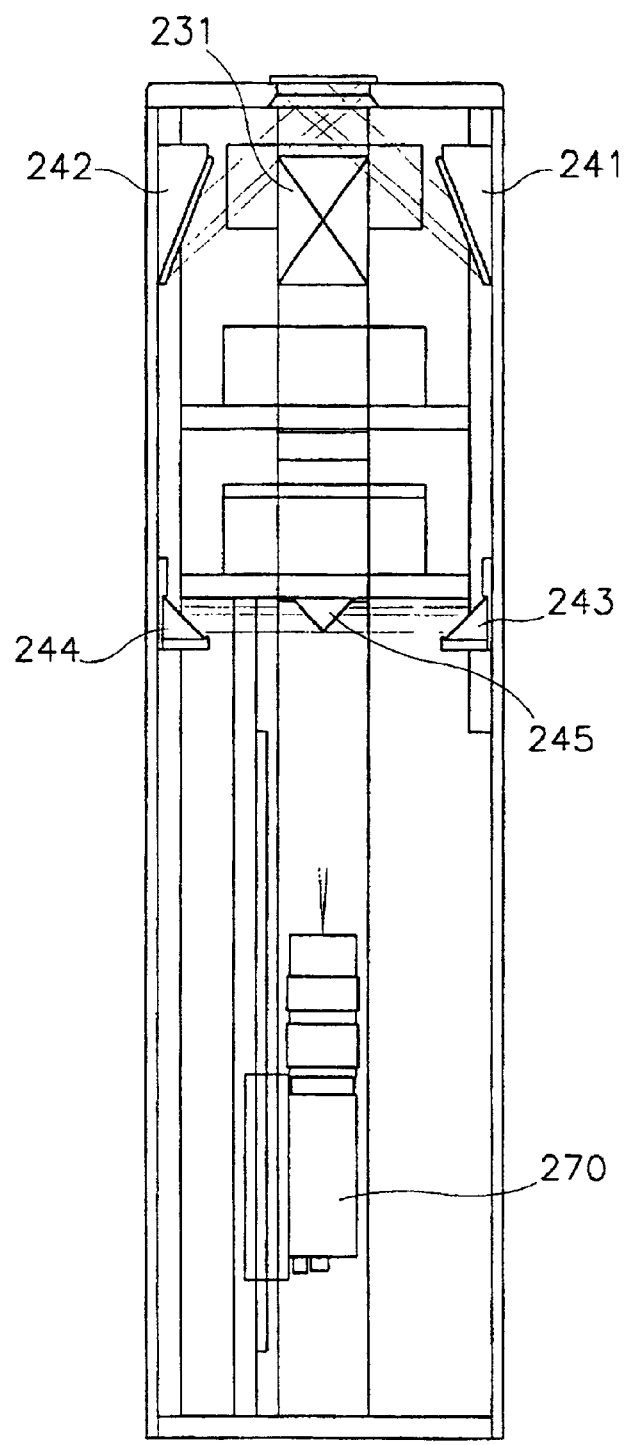
FIG. 11 is a drawing for illustrating passages where images of a second side view and a fourth side view of an electronic component lead are transmitted in acquiring means according to the first embodiment of the present invention.

Furthermore, the image transfer means 210 is arranged, as illustrated in FIGS. 9, 10 and 11, with first image transfer means 221 and 222 for transmitting to the first camera 250 a bottom view image of the electronic component package 100 which is horizontally moved by the pickup header 105 or the tray 700, second image transfer means 231~237 for combining images of first side view and third side view of the electronic component package 100 to transfer same to the second camera 260 and third image transfer means 241~245 for combining images of second and fourth side views of the electronic component package 100 to transfer same to the third camera 270.

Furthermore, the first image transfer means 221 and 222 include, as illustrated in FIG. 9, a first reflecting mirror 221 for reflecting a bottom view image of the electronic component package 100 to a second reflecting mirror 222, and a second reflecting mirror 222 for reflecting the image reflected from the first reflecting mirror 221 to the first camera 250.

The second image transfer means 231~237 are installed with, as illustrated in FIG. 10, third and fourth reflecting mirrors 231 and 232 for respectively reflecting images from first side view and third side view of the electronic component package 100 to first and second right angle prisms 233 and 234, first and second right angle prisms 233 and 234 for reflecting to a third right angle prism 235 the images of the first and third side views respectively reflected from the third and fourth reflecting mirrors 231 and 232, a third right angle prism 235 for combining the images respectively reflected from the first and second right angle prisms 233 and 234, the fifth reflecting mirror 236 for reflecting the images combined by the third right angle prism 235 to a sixth reflecting mirror 237, and the sixth reflecting mirror 237 for reflecting the images reflected by the fifth reflecting mirror 236 back to the second camera 260.

Furthermore, third image transfer means 241~245 include, as illustrated in FIG. 11, seventh and eighth reflecting mirrors 241 and 242 for respectively reflecting images of second side view and fourth side view of the electronic component package 100 to fourth and fifth right angle prisms 243 and 244, the fourth and fifth right angle prisms 243 and 244 for reflecting the images of the second side view and fourth side view reflected from the seventh and eighth reflecting mirrors 241 and 242 back to sixth right angle prism 245, and the sixth right angle prism 245 for combining the images reflected from the fourth and fifth right angle prisms 243 and 244 to reflect same to the third camera 270.

At this time, the first~sixth right angle prisms (233, 234, 235, 243, 244 and 245) are all coated at reflecting surfaces thereof with full reflecting coating material (such as aluminum coating), such that the same effect accomplished by using the right angle prisms can be obtained if reflecting mirrors are used instead of the first~sixth right angle prisms (233, 234, 235, 243, 244 and 245).

Figure 12A:
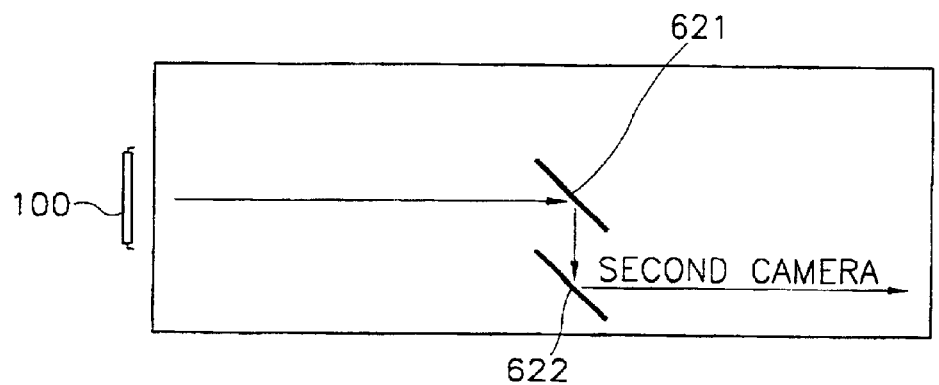
FIGS. 12a, 12b and 12c are drawings for illustrating passages where bottom view and side view images of an electronic component lead are transmitted in acquiring means according to the second embodiment of the present invention.
Figure 12B:
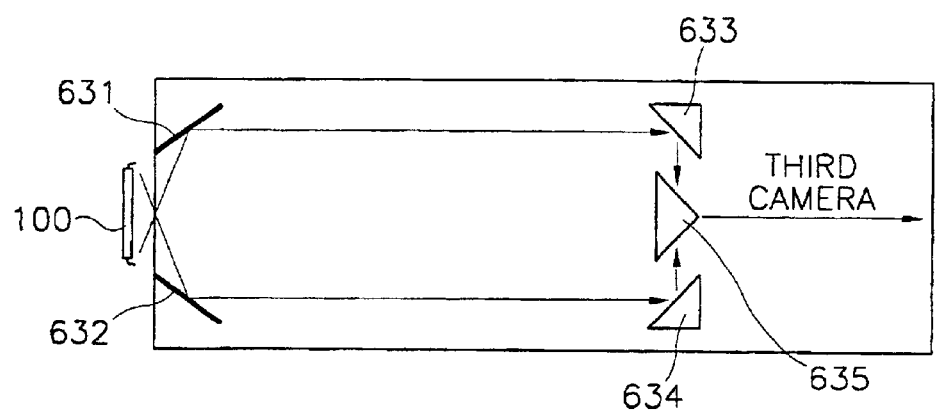
Figure 12C:
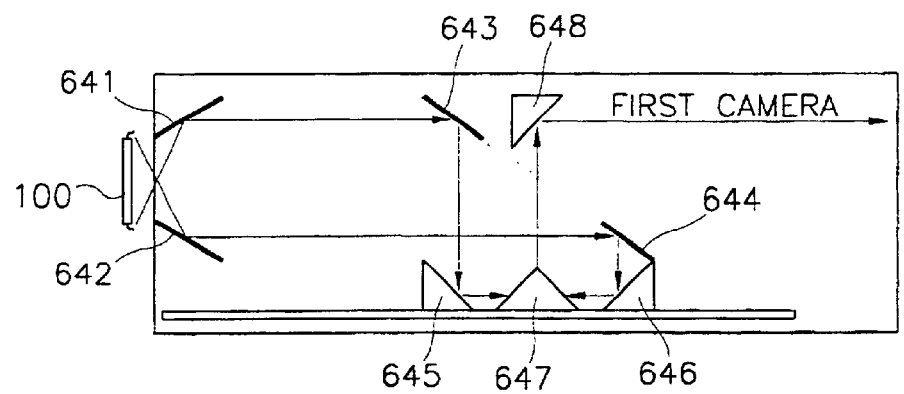

Meanwhile, image transfer means 210 according to a second embodiment of the present invention is disposed with, as illustrated in FIGS. 12a, 12b and 12c, first image transfer means 621 and 622 for transmitting to the second camera 260 a bottom view image of the electronic component package 100 horizontally moved by the pickup header 105 or the tray 700, second image transfer means (631, 632, 633, 634 and 635) for combining images of first side view and third side view of the electronic component package 100 to transmit same to the third camera 270, and third image transfer means (641~648) for combining images of second side view and fourth side view of the electronic component package 100 to transfer same to the first camera 250.

Furthermore, the first image transfer means 621 and 622 include, as illustrated in FIG. 12a, a first reflecting mirror 621 for reflecting a bottom view image of the electronic component package 100 to the second reflecting mirror 622 and a second reflecting mirror 622 for reflecting the image reflected from the first reflecting mirror 621 to the second camera 260.

The second image transfer means (631~635) include, as illustrated in FIG. 12b, third and fourth reflecting mirrors 631 and 632 for respectively reflecting images of first side view and third side view at the electronic component package 100 to the first and second right angle prisms 633 and 634, first and second right angle prisms 633 and 634 for reflecting the images of first side view and third side view respectively reflected from the third and fourth reflecting mirrors 631 and 632 to the third right angle prism 635, and third right angle prism 635 for combining the images respectively reflected from the first and second right angle prisms 633 and 634 to reflect same to the third camera 270.

Furthermore, the third image transfer means (641~648) include, as illustrated in FIG. 12c, fifth and sixth reflecting mirrors 641 and 642 for respectively reflecting images of second and fourth side views at the electronic component package 100 to seventh and eighth reflecting mirrors 643 and 644, seventh and eighth reflecting mirrors 643 and 644 for reflecting the images of the second and fourth side views reflected from the fifth and sixth reflecting mirrors 641 and 642 again to fourth and fifth right angle prisms 645 and 646, fourth and fifth right angle prisms 645 and 646 for reflection images of the second and fourth side views reflected from the seventh and eighth reflecting mirrors 643 and 644 to the sixth right angle prism 647, a sixth right angle prism 647 for combining images reflected from the fourth and fifth right angle prisms 645 and 646 to reflect same to the seventh right angle prism 648, and a seventh right angle prism 648 for reflecting the image reflected from the sixth right angle prism 647 to the first camera 250.

Figure 13:
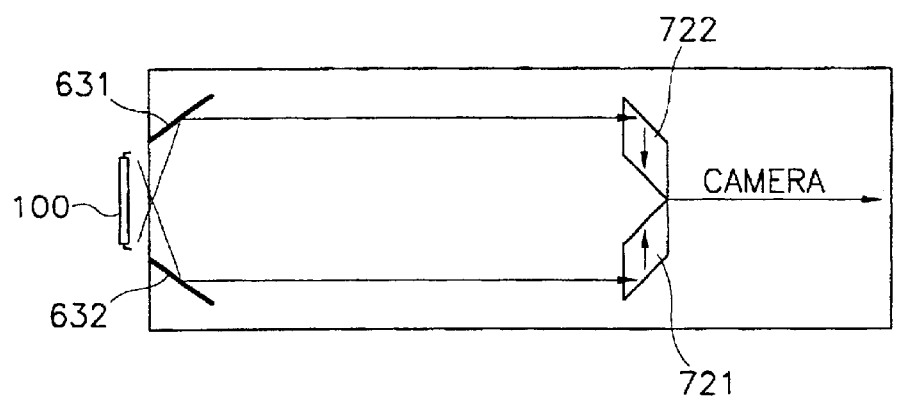
FIG. 13 is a drawing for illustrating a passage where a side view image of an electronic component lead is transmitted in acquiring means according to a third embodiment of the present invention.

Meanwhile, image transfer means 210 according to a third embodiment of the present invention is the same as illustrated in FIG. 13, except that trapezoid prisms 721 and 722 are used when compared with the image transfer means 210 shown in FIGS. 9, 10, 11 and 12.

In other words, the trapezoid prisms 721 and 722 are used for combination of images instead of the first, second and third right angle prisms 233, 234 and 235 shown in FIGS. 9 and 10, the fourth, fifth and sixth right angle prisms 243, 244 and 245 illustrated in FIG. 11, the first, second and third right angle prisms 633, 634 and 635 given in FIG. 12b and the fourth, fifth and sixth right angle prisms 645, 646 and 647 illustrated in FIG. 12c.

Now, operational effect of the electronic component lead inspection device thus constructed according to the embodiment of the present invention will be described.

In the electronic component lead inspection device according to the first, second and third embodiments of the present invention, when an electronic component lead inspection is started, the pickup header 105 picks up the electronic component package 100 to horizontally move same, and the position detecting means 300 detects a position of the electronic component package 100 horizontally moved by the pickup header 105 to output same to the control means 400.

The control means 400 controls the first light source 115 or the second light source 120 to illuminate light when a signal is input from the position detecting means 300 that the electronic component package 100 has arrived at a acquiring position.

In other words, the control means 400 controls the first light source 115 to illuminate the light when the electronic component package 100 horizontally moved by the pickup header 105 is the gull wing type electronic component package, and controls the second light source 120 to illuminate the light when the electronic component package 100 horizontally moved by the pickup header 105 is BGA type electronic component package.

Successively, when the gull wing type electronic component package reaches the acquiring position, the first light source 115 illuminates the light to the reflecting plate 110, such that portion of the electronic component package 100 becomes dark while other background gets brightened.

Furthermore, when the BGA type electronic component package arrives at the acquiring position, the second light source 120 illuminates the light to the electronic component package 100 to brighten a portion of the electronic component package lead.

Meanwhile, in the electronic component lead inspection device according to the fourth embodiment of the present invention, when an electronic component lead inspection is started, the tray 700 accommodated with the electronic component package 100 is horizontally moved and the position detecting means 300 detects a position of the electronic component package 100 horizontally moved by the tray 700 to output same to the control means 400. When a signal is input from the position detecting means 300 that the electronic component package 100 has reached the acquiring position, the control means 400 controls the light source 710 to illuminate the light.

At this time, in the electronic component lead inspection device according to the first, second, third and fourth embodiments of the present invention, the acquiring means 200 disposed above or underneath the passage of the moving electronic component package 100 outputs to the control signal an image signal that has acquired bottom view and side views of the electronic component package 100, and the control means 400 outputs the image signal input from the acquiring means 200 to the inspecting and displaying means 500, while the inspection and displaying means 500 receives the image signal from the control means 400 to inspect and display the images of bottom view and side views of the electronic component package 100 horizontally moved by the pickup header 105 or the tray 700.

Meanwhile, the acquiring means 200 is equipped with first, second and third cameras 250, 260 and 270 for acquiring bottom view and side views of the electronic component package 100 transmitted by the image transfer means 210, where, only a height adjustment of the third camera 270 will be described by way of example, because height adjustments of the first, second and third cameras 250, 260 and 270 are all the same.

In order to adjust the height of the third camera 270, first of all, fixing means 278 is manipulated to allow the third camera 270 to move upwardly and downwardly. Then, the guide plate 277 integrally formed with the third camera 270 is made to slide upwardly and downwardly along the guide rail 276 to adjust the height of the third camera 270, and again, the fixing means 278 is manipulated to fix the third camera 270.

Hereinafter, a process, where the image transfer means 210 transfer the images of the electronic component package 100 in bottom view and side views to the first, second and third cameras 250, 260 and 270, will be described in detail with reference to FIGS. 9, 10 and 11.

As illustrated in FIG. 9, a bottom view image of the electronic component package 100 horizontally moved by the pickup header 105 or the tray 700 is reflected by the first reflecting mirror 221 to thereafter be transmitted to and reflected from the second reflecting mirror 222, and to be transmitted to the first camera 250, such that the first camera 250 can acquire the bottom view image of the electronic component package 100.

Furthermore, as illustrated in FIG. 10, the images of first and third side views of the electronic component package 100 horizontally moved by the pickup header 105 or the tray 700 are reflected by the third and fourth reflecting mirrors 231 and 232 to be transmitted to the first and second right angle prisms 233 and 234, and the images of first and third side views of the electronic component package 100 respectively reflected from the third and fourth reflecting mirrors 231 and 232 are reflected from the first and second right angle prisms 233 and 234 to thereafter be transmitted to the third right angle prism 235.

The images of first and third side views of the electronic component package 100 reflected from the first and second right angle prisms 233 and 234 are combined by the third right angle prism 235 to thereafter be transmitted to the fifth reflecting mirror 236, where the images combined by the third right angle prism 235 are reflected by the fifth reflecting mirror 236 to thereafter be transferred to the sixth reflecting mirror 237.

The images reflected by the fifth reflecting mirror 236 is again reflected by the sixth reflecting mirror 237 to be transmitted to the second camera 260 which, in turn, acquires the images of the first and third side views of the electronic component package 100.

Furthermore, as illustrated in FIG. 11, images of the second and fourth side views of the electronic component package 100 horizontally moved by the pickup header 105 or the tray 700 are reflected from the seventh and eight reflecting mirrors 241 and 242 to be transmitted to the fourth and fifth right angle prisms 243 and 244, where the images of the second and fourth side views of the electronic component package 100 reflected from the seventh and eighth reflecting mirrors 241 and 242 are again reflected by the fourth and fifth right angle prisms 243 and 244 to thereafter be transmitted to the sixth right angle prism 245.

The images reflected from the fourth and fifth right angle prisms 243 and 244 are combined by the sixth right angle prism 245 to be transferred to the third camera 270, where the third camera 270 acquires the images of the second and fourth side views of the electronic component package 100.

Figure 14A:
FIGS. 14a, 14b and 14c are drawings for illustrating bottom view and side view images of a gull wing type electronic component package acquired by an electronic component lead inspection device according to the present invention.
Figure 14B:
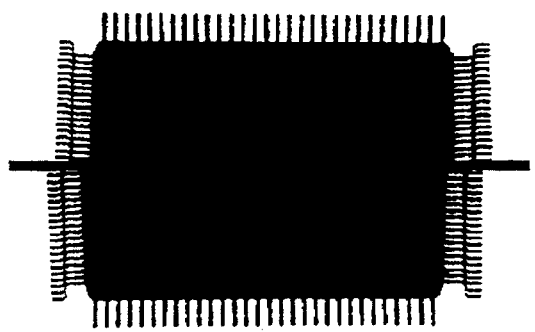
Figure 14C:
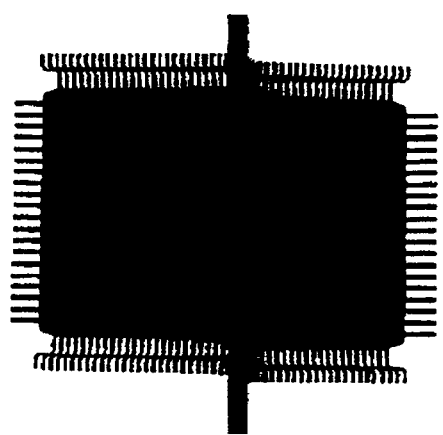

At this time, if the electronic component package 100 horizontally moved by the pickup header 105 is the gull wing type electronic component package, the image acquired by the first camera 250 becomes a bottom view of the electronic component package 100, as illustrated in FIG. 14*a*, the image acquired by the second camera 260 becomes an image combined by the first and third side views of the electronic component package 100, as illustrated in FIG. 14*b*, and the image acquired by the third camera 270 becomes on image combined by the second and fourth side views of the electronic component package 100, as illustrated in FIG. 14*c*.

Figure 15A:
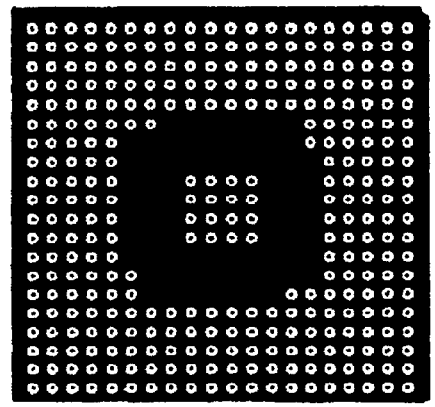
FIGS. 15a, 15b and 15c are drawings for illustrating bottom view and side view images of a ball grid array type electronic component package acquired by an electronic component lead inspection device according to the present invention.
Figure 15B:
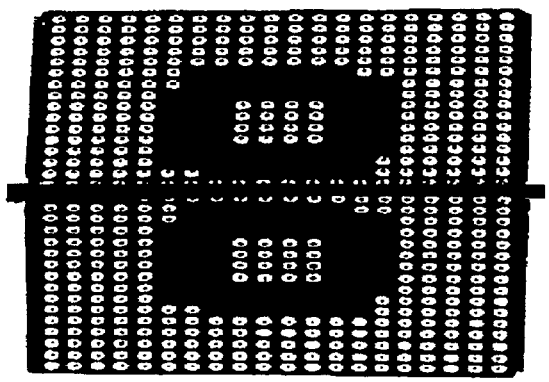
Figure 15C:
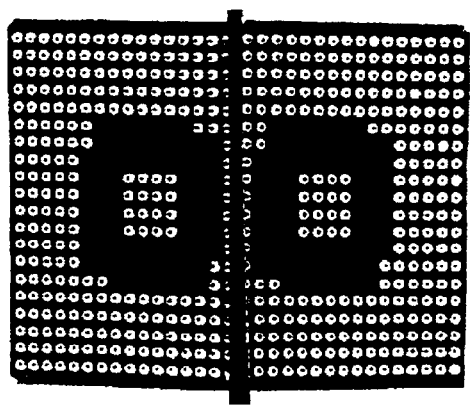

Furthermore, if the electronic component package 100 horizontally moved by the pickup header 105 is a BGA type electronic component package, the image acquired by the first camera 250 becomes a bottom view of the electronic component package 100, as illustrated in FIG. 15*a*, the image acquired by the second camera 260 becomes an image combined by images from the first and third side views of the electronic component package 100 as illustrated in FIG. 15*b*, and the image acquired by the third camera 270 is an image combined by images from the second and fourth side views of the electronic component package 100, as illustrated in FIG. 15*c*.

Successively, a process where image transfer means 210 according to the second embodiment of the present invention transfers the images of bottom and side views of the electronic component package 100 to the first, second and third cameras 250, 260 and 270 will be described in detail with reference to FIGS. 12*a*, 12*b* and 12*c*.

As illustrated in FIG. 12*a*, a bottom view of the electronic component package 100 horizontally moved by the pickup header 105 or the tray 700 is sequentially reflected by the first and second reflecting mirrors 621 and 622 to be transmitted to the second camera 260, such that the second camera 260 becomes to acquire the bottom view of the electronic component package 100.

Furthermore, as illustrated in FIG. 12*b*, images of first and third side views of the electronic component package 100 horizontally moved by the pickup header 105 or the tray 700 are reflected by the third and fourth reflecting mirrors 631 and 632 and by the first and second right angle prisms 633 and 634 to thereafter be transmitted to the third right angle prism 635, and the third camera 270 becomes to acquire the images of the first and third side views of the electronic component package 100 as images of the first and third side views of the electronic component package 100 are combined by the third right angle prism 635 to thereafter be transferred to the third camera 270.

Successively, as illustrated in FIG. 12*c*, images of second and fourth side views of the electronic component package 100 horizontally moved by the pickup header 105 or the tray 700 are respectively reflected by the fifth and sixth reflecting mirrors 641 and 642, the seventh and eight reflecting mirrors 643 and 644, and the fourth and fifth right angle prisms 645 and 646 to thereafter be transmitted to the sixth right angle prism 647, where the sixth right angle prism 647 combines the images reflected by the fourth and fifth right angle prisms 645 and 646 to be transferred to the seventh prism 648, and the seventh right angle prism 648 reflects the image transmitted from the sixth right angle prism 647 to transfer same to the first camera 250, such that the first camera 250 can acquire the images of the second and fourth side views of the electronic component package 100.

At this time, if the electronic component package 100 horizontally moved by the pickup header 105 is a gull wing type electronic component package, the image acquired by the second camera 260 becomes a bottom view of the electronic component package 100 as illustrated in FIG. 14*a*, the image acquired by the third camera 270 becomes an image combined from the first and third side views of the electronic component package 100 as illustrated in FIG. 14*b*, and the image acquired by the first camera 250 becomes an image combined from the second and fourth side views of the electronic component package 100 as illustrated in FIG. 14*c*.

Furthermore, if the electronic component package 100 horizontally moved by the pickup header 105 is BGA type electronic component package, an image acquired by the second camera 260 becomes a bottom view of the electronic component package 100 as illustrated in FIG. 15*a*, an image acquired by the third camera 270 becomes an image combined from the first and third side views of the electronic component package 100 as illustrated in FIG. 15*b*, and an image acquired by the first camera 250 becomes an image combined from the second and fourth side views of the electronic component package 100 as illustrated in FIG. 15*c*.

As apparent from the foregoing, there is an advantage in the present invention thus described in that an electronic component package being picked up, moved, inspected and produced can be all inspected on real time and there is no damage caused to an electronic component lead either.

Furthermore, there is another advantage in that a three-dimensional lead inspect using stereo vision method is possible on the bail grid array type electronic component package and the gull wing type electronic component package by way of one inspection device. There is still another advantage in that inspects on the coplanarity, warpage, mold damage and the like can be performed and the present invention can be used in easy coupling to an existing electronic component device.

What is claimed is:

1. An electronic component lead inspection device, the device comprising:
    a pickup header for picking up an electronic component package to move same;
    a reflecting plate attached to the pickup header;
    a first light source for illuminating a light to the reflecting plate;
    a second light source for illuminating a light to the electronic components package;
    acquiring means for acquiring an image of the electronic component package underneath a traveling passage of the electronic component package;
    control means for controlling the first light source to illuminate a light if the electronic component package is a gull wing type electronic component package and for controlling the second light source to illuminate a light if the electronic components package is a ball grid array type electronic component package and for outputting an image signal of the electronic component package acquired by the acquiring means; and
    inspecting and displaying means for receiving the image signal of the electronic component package output from the control means to inspect and display the image of the electronic component package.

2. An electronic component lead inspection device, the device comprising:
    (A) a light source for illuminating a light to an electronic component package;
    (B) acquiring means for acquiring an image of the electronic component package, the acquiring means comprises:
        (a) image transfer means for transmitting images of bottom view and side view of the electronic component package, the image transfer means comprises:
            a first image transfer means for transmitting an image of bottom view of the electronic component package, and
            second and third image transfer means for combining images of mutually facing side views of the electronic component package to thereafter transfer same, and
        (b) one or more cameras for acquiring the images of bottom view and side views of the electronic component package transferred through the image transfer means;
    (C) control means for outputting an image signal of the electronic component package acquired by the acquiring means; and
    (D) inspecting and displaying means for receiving the image signal of the electronic component package output from the control means to inspect and display the image of the electronic component package.

3. The electronic component lead inspection device as defined in claim 2, wherein the first image transfer means comprises one or more reflecting mirrors for reflecting the image of bottom view of the electronic component package to thereafter transfer same to the camera.

4. The electronic lead inspection device as defined in claim 3, wherein the second and third image transfer means comprise:
    two or more reflecting mirrors for respectively reflecting images of mutually facing side views of the electronic component package; and
    one or more right angle prisms for combining images respectively reflected by the reflecting mirrors to the one camera.

5. The electronic component lead inspection device as defined in claim 2, wherein the acquiring means comprises:
    a first camera for acquiring the image of bottom view of the electronic component package transmitted from the first image transfer means; and
    second and third cameras for acquiring respective the images of side views of the electronic component package combined and transmitted thereafter by the second and third image transfer means.

6. The electronic component lead inspection device as defined in claim 2, wherein the acquiring means further comprises a height adjusting means for adjusting heights of the camera.

7. The electronic component lead inspection device as defined in claim 6, wherein the height adjusting means comprises:
    a guide rail formed at one side of a housing;
    a guide plate integrally formed at the camera to upwardly and downwardly move the camera along the guide rail; and
    fixing means for fixing the guide plate to the guide rail to thereby fix a position of the camera.

8. An electronic component lead inspection device, the device comprising:
    (A) a light source for illuminating a light to an electronic component package;
    (B) acquiring means for acquiring an image of the electronic component package, the acquiring means comprises:
        (a) image transfer means disposed on an upper of a housing to transfer images of bottom and side views of the electronic component package, and
        (b) first, second and third cameras provided underneath the housing to respectively acquire bottom and side views of the electronic component package transmitted via the image transfer means, the image transfer means comprises:
            a pair of reflecting mirrors centrally arranged at a housing for twice reflecting at right angle a bottom view of the electronic component package to thereafter transfer same to the first camera,
            four reflecting mirrors respectively disposed at four side views of the housing to reflect four side views of the electronic component package lengthwise of the housing,
            four right angle prisms mounted at four side views of the housing to respectively face the four reflecting mirrors to reflect at right angle the images of four side views reflected from the four reflecting mirrors relative to lengthwise direction of the housing, and
            two right angle prisms respectively disposed between two facing right angle prisms out of the four right angle prisms to combine images of two side views of the two facing electronic component package and to respectively transfer same to the second and third cameras;
    (C) control means for outputting an image signal of the electronic component package acquired by the acquiring means; and
    (D) inspecting and displaying means for receiving the image signal of the electronic component package output from the control means to inspect and display the image of the electronic component package.

9. An electronic component lead inspection device, the device comprising:
   (A) a light course for illuminating a light to an electronic component package;
   (B) acquiring means for acquiring an image of the electronic component package, the acquiring means comprises:
      (a) image transfer means for combining images of mutually facing side views of the electronic component package to thereafter transfer same to a camera, and
      (b) one or more cameras for acquiring the images of side views of the electronic component package transferred through the image transfer means;
   (C) control means for outputting an image signal of the electronic component package acquired by the acquiring means; and
   (D) inspecting and displaying means for receiving the image signal of the electronic component package output from the control means to inspect and display the image of the electronic component package.

* * * * *